(12) United States Patent
Ponnaiah et al.

(10) Patent No.: US 10,774,041 B2
(45) Date of Patent: Sep. 15, 2020

(54) PROCESS FOR THE PREPARATION OF APREMILAST

(71) Applicant: Davuluri Ramamohan Rao, Hyderabad (IN)

(72) Inventors: Ravi Ponnaiah, Madurai (IN); Praveen Kumar Neela, Hyderabad (IN); Madanlal Anandkumar Lahoti, Nandurbar (IN); Srinivas Pardha Gavini Saradhi, Andhra Pradesh (IN)

(73) Assignee: Davuluri Ramamohan Rao, Hyderabad (IN)

( * ) Notice: Subject to any disclaimer, the term of this patent is extended or adjusted under 35 U.S.C. 154(b) by 0 days.

(21) Appl. No.: 16/093,653

(22) PCT Filed: Jan. 27, 2017

(86) PCT No.: PCT/IN2017/000022
§ 371 (c)(1),
(2) Date: Oct. 15, 2018

(87) PCT Pub. No.: WO2017/179065
PCT Pub. Date: Oct. 19, 2017

(65) Prior Publication Data
US 2019/0071401 A1    Mar. 7, 2019

(30) Foreign Application Priority Data

Apr. 15, 2016    (IN) .............................. 201641013369

(51) Int. Cl.
| | | |
|---|---|---|
| *C07D 209/48* | (2006.01) | |
| *C07C 253/30* | (2006.01) | |
| *C07C 315/04* | (2006.01) | |

(52) U.S. Cl.
CPC .......... *C07D 209/48* (2013.01); *C07C 253/30* (2013.01); *C07C 315/04* (2013.01)

(58) Field of Classification Search
None
See application file for complete search history.

(56) References Cited

U.S. PATENT DOCUMENTS

| | | |
|---|---|---|
| 8,242,310 B2 | 8/2012 | Saindane et al. |
| 2012/0329696 A1 | 12/2012 | Denutte |
| 2013/0217919 A1 | 8/2013 | Connolly et al. |
| 2014/0081032 A1 | 3/2014 | Connolly et al. |

FOREIGN PATENT DOCUMENTS

| | | |
|---|---|---|
| EP | 2431371 A1 | 3/2012 |
| WO | WO2010119877 A1 | 10/2010 |

OTHER PUBLICATIONS

Office Action dated Oct. 10, 2019 for Indian Patent Application No. 201641013369.

*Primary Examiner* — Po-Chih Chen
(74) *Attorney, Agent, or Firm* — Ling Wu; Stephen Yang; Ling and Yang Intellectual Property

(57) ABSTRACT

The present invention relates to an improved process for the preparation of Apremilast of formula (I).

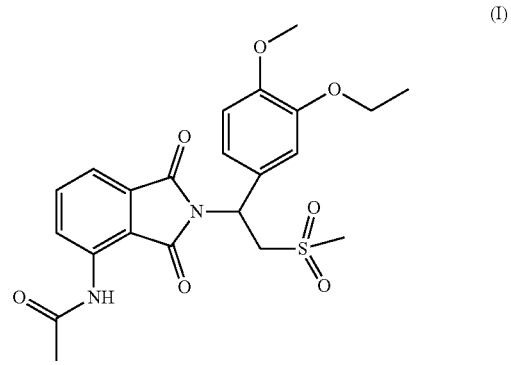

6 Claims, 3 Drawing Sheets

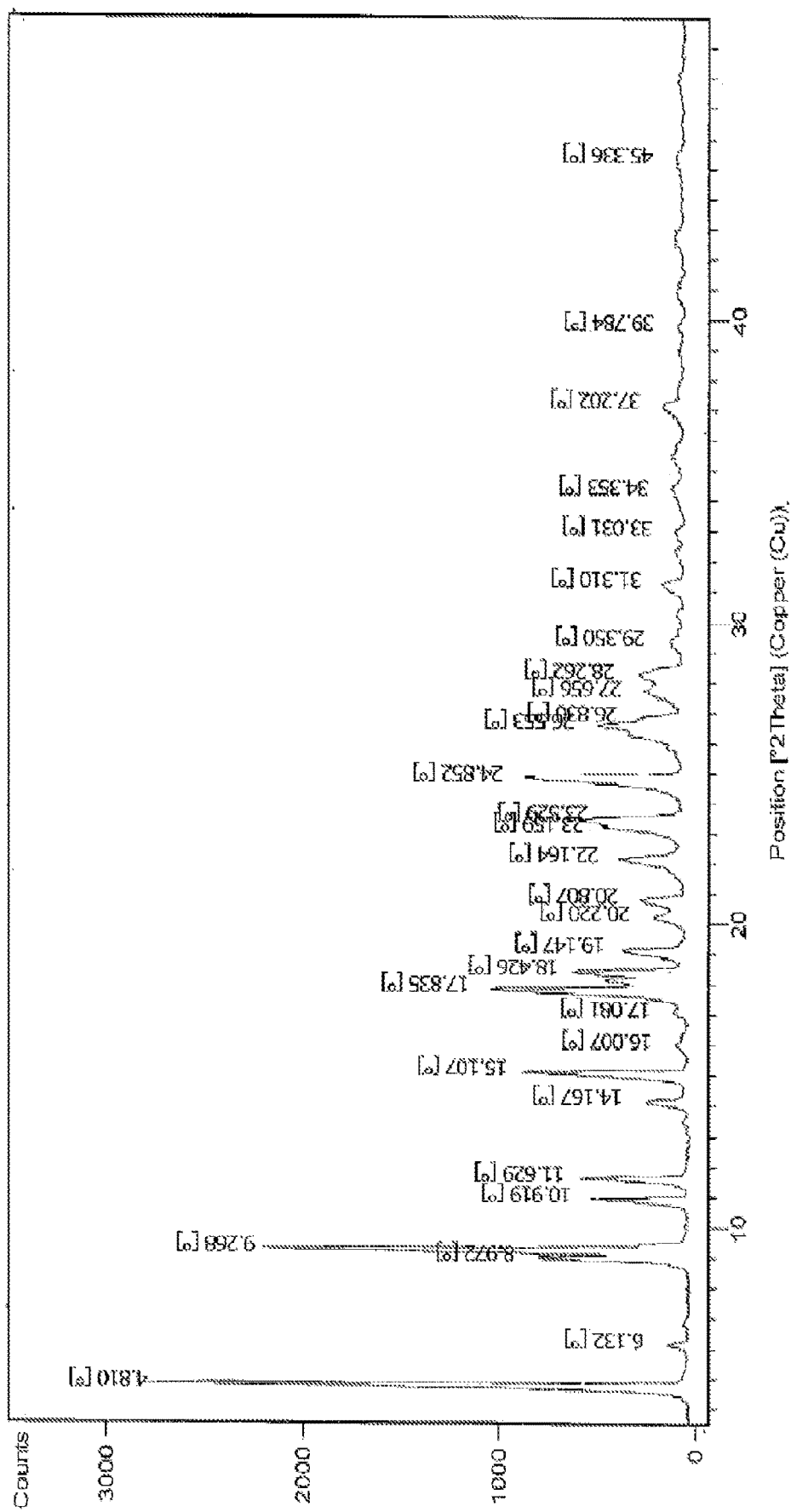
Figure II

| Pos. [°2Th.] | d-spacing [Å] | Area [cts*°2Th.] | Height [cts] | Rel. Int. [%] |
|---|---|---|---|---|
| 4.8104 | 18.37038 | 303.94 | 2631.34 | 100.00 |
| 6.1323 | 14.41313 | 20.02 | 110.31 | 4.19 |
| 8.9723 | 9.85630 | 75.24 | 759.98 | 28.88 |
| 9.2676 | 9.54285 | 241.14 | 2087.64 | 79.34 |
| 10.9195 | 8.10266 | 69.95 | 471.04 | 17.90 |
| 11.6290 | 7.60985 | 67.25 | 509.40 | 19.36 |
| 14.1675 | 6.25153 | 35.06 | 212.45 | 8.07 |
| 15.1071 | 5.86474 | 170.53 | 794.93 | 30.21 |
| 16.0074 | 5.53686 | 12.68 | 64.03 | 2.43 |
| 17.0809 | 5.19123 | 13.90 | 70.22 | 2.67 |
| 17.8348 | 4.97345 | 97.13 | 980.99 | 37.28 |
| 18.4262 | 4.81514 | 106.06 | 535.60 | 20.35 |
| 19.1471 | 4.63544 | 39.02 | 295.58 | 11.23 |
| 20.2197 | 4.39191 | 25.00 | 168.36 | 6.40 |
| 20.8075 | 4.26915 | 53.00 | 229.42 | 8.72 |
| 22.1640 | 4.01084 | 74.94 | 324.37 | 12.33 |
| 23.1587 | 3.84076 | 52.16 | 395.14 | 15.02 |
| 23.5293 | 3.78111 | 62.58 | 379.26 | 14.41 |
| 24.8516 | 3.58284 | 93.02 | 805.30 | 30.60 |
| 26.5527 | 3.35703 | 80.81 | 445.21 | 16.92 |
| 26.8302 | 3.32294 | 30.31 | 229.64 | 8.73 |
| 27.6564 | 3.22553 | 53.77 | 203.65 | 7.74 |
| 28.2622 | 3.15775 | 55.60 | 240.65 | 9.15 |
| 29.3501 | 3.04313 | 31.66 | 79.94 | 3.04 |
| 31.3100 | 2.85697 | 19.67 | 99.35 | 3.78 |
| 33.0314 | 2.71192 | 11.44 | 43.32 | 1.65 |
| 34.3526 | 2.61057 | 23.34 | 58.93 | 2.24 |
| 37.2024 | 2.41689 | 28.99 | 97.59 | 3.71 |
| 39.7839 | 2.26581 | 9.44 | 23.85 | 0.91 |
| 45.3358 | 1.99875 | 21.93 | 33.59 | 1.28 |

Figure III

PROCESS FOR THE PREPARATION OF APREMILAST

FIELD OF THE INVENTION

The present invention relates to an improved process for the preparation of Apremilast of formula (I).

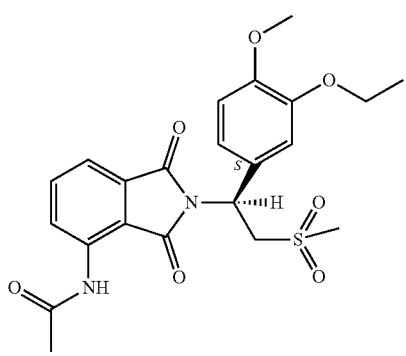

(I)

BACKGROUND OF THE INVENTION

Apremilast, chemically known as N-(2-((1S)-1-(3-ethoxy-4-methoxyphenyl)-2-(methylsulfonyl) ethyl)-2,3-dihydro-1,3-dioxo-1H-isoindol-4-yl)-acetamide, is represented by formula (I).

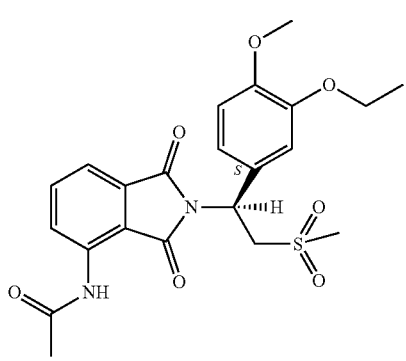

(I)

It is an anti-inflammatory drug, specifically inhibits PDE4 and also inhibits spontaneous production of TNF-alpha from human rheumatoid synovial cells.

Apremilast is first disclosed in U.S. Pat. No. 6,020,358. It also describes process for the preparation of Apremilast, which involves coupling of 3-acetamido phthalic anhydride and 1-(3-alkoxy-4-alkoxyphenyl)-2-(methylsulfonyl) ethanamine in the presence of acetic acid, followed by resolution using chromatography.

The process for preparation of Apremilast of formula (I) is also disclosed in WO2012083153A1, WO2013126360, WO2013126495, U.S. Pat. Nos. 7,427,638, 8,242,310, CN 104761474, CN 104803897 and CN 103864670.

The process disclosed in the above mentioned patents/patent applications is having following disadvantages:
a) Use of Lithium hexamethyl disilazide is hazardous and reports lower yield (Yield=39%).
b) Use of very expensive reagents like (R, S)-t-Bu-Josiphos or Rh (cod)$_2$ OTf.
c) Purification by using column chromatography techniques, which is very difficult in commercial scale.
d) Low yield & Low purity.

In view of the preparation methods available for Apremilast, there is a need for simple and cost effective process for the preparation of Apremilast with high optical purity by avoiding the use of expensive starting raw materials.

OBJECTIVE OF THE INVENTION

The main objective of the invention is to provide an improved process for the preparation of Apremilast having formula (I).

Another objective of the invention is to provide a simple and cost effective process for the preparation of Apremilast with high optical purity.

Further objective of the invention is to provide an industrially viable process for the preparation of Apremilast avoiding expensive raw materials.

SUMMARY OF THE INVENTION

Accordingly, the present invention provides an improved process for the preparation of Apremilast of formula (I),

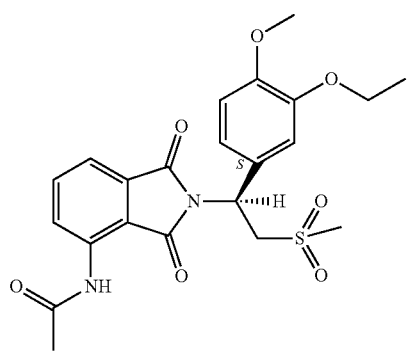

(I)

which comprises:
i) reacting ethyl vanillin of formula (II)

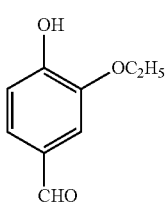

(II)

with hydroxylamine, or its salt in a solvent to obtain 3-ethoxy-4-hydroxybenzonitrile of formula (III);

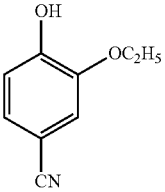

(III)

ii) methylating 3-ethoxy-4-hydroxybenzonitrile of formula (III) with O-methylating reagent in a solvent in the presence of a base to obtain 3-ethoxy-4-methoxybenzonitrile of formula (IV);

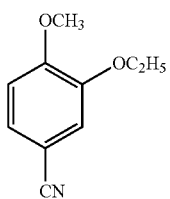
(IV)

iii) reacting 3-ethoxy-4-methoxybenzonitrile of formula (IV) with dimethyl sulfone and n-butyl lithium (n-BuLi) in hexane in a solvent to obtain (E/Z)-1-(3-ethoxy-4-methoxyphenyl)-2-(methylsulfonyl) ethenamine of formula (V);

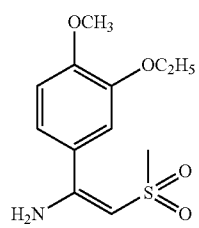
(V)

iv) reducing (E/Z)-1-(3-ethoxy-4-methoxyphenyl)-2-(methylsulfonyl) ethenamine of formula (V) with reducing agent and chiral auxiliary in a solvent to obtain 1-(3-ethoxy-4-methoxyphenyl)-2-(methylsulfonyl) ethanamine of formula (VI);

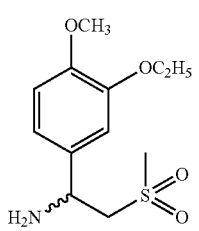
(VI)

v) reacting 1-(3-ethoxy-4-methoxyphenyl)-2-(methylsulfonyl) ethanamine of formula (VI) with N-acetyl-L-valine in a solvent to obtain (1S)-1-(3-ethoxy-4-methoxyphenyl)-2-(methylsulfonyl) ethenamine-N-acetyl-L-valine salt of formula (VII) having chiral purity greater than 99.8%;

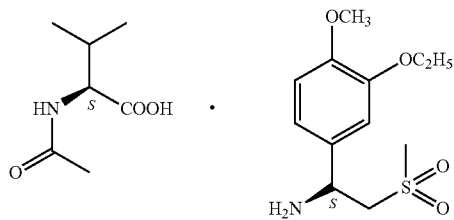
(VII)

vi) reacting (1S)-1-(3-ethoxy-4-methoxyphenyl)-2-(methylsulfonyl) ethenamine-N-acetyl-L-valine salt of formula (VII) with 3-acetamino phthalic anhydride of formula (VIII)

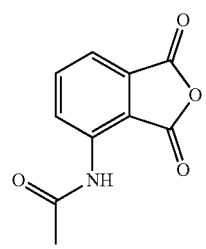
(VIII)

in the presence of acetic acid in a solvent to obtain crude Apremilast of formula (IX);

vii) Purifying crude Apremilast of formula (IX) with mixed solvent to obtain Apremilast of formula (I).

In another aspect, the present invention provides a novel process for the preparation of 3-ethoxy-4-methoxybenzonitrile of formula (IV)

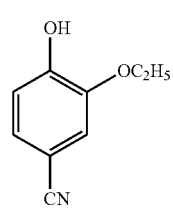
(IV)

which comprises:

methylating 3-ethoxy-4-hydroxybenzonitrile of formula (III)

(III)

with O-methylating reagent in a solvent in the presence of a base to obtain 3-ethoxy-4-methoxybenzonitrile of formula (IV).

In another aspect, the present invention provides an improved process for the preparation of 1-(3-ethoxy-4-methoxyphenyl)-2-(methylsulfonyl) ethanamine of formula (VI).

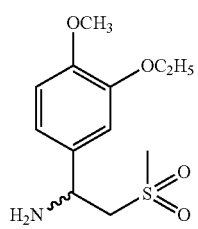

which comprises:

reducing (E/Z)-1-(3-ethoxy-4-methoxyphenyl)-2-(methylsulfonyl) ethenamine of formula (V)

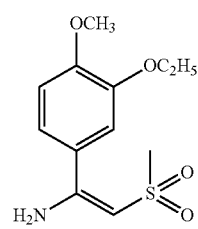

with reducing agent & chiral auxiliary in a solvent to obtain 1-(3-ethoxy-4-methoxyphenyl)-2-(methylsulfonyl) ethanamine of formula (VI).

In yet another aspect, crystalline form of (1S)-1-(3-ethoxy-4-methoxyphenyl)-2-(methylsulfonyl) ethenamine-N-acetyl-L-valine salt having the following structural formula (VII)

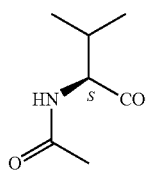 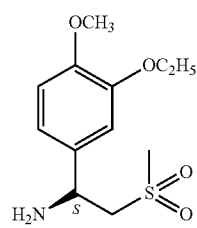

characterized by its powder X-ray diffraction peaks at 18.3, 14.4, 9.8, 9.5, 8.1, 7.6, 6.2, 5.8, 5.5, 5.1, 4.9, 4.8, 4.6, 4.3, 4.2, 4.0, 3.8, 3.7, 3.5, 3.3, 3.2, 3.1, 3.0, 2.8, 2.7, 2.6, 2.4, 2.2 and 1.9±0.2 degrees 2θ.

BRIEF DESCRIPTION OF THE DRAWINGS

FIG. I: Illustrates the Differential Scanning calorimetry of crystalline (1S)-1-(3-ethoxy-4-methoxyphenyl)-2-(methylsulfonyl) ethenamine-N-acetyl-L-valine salt of formula (VII).

FIG. II: illustrates the powder X-ray diffraction pattern of crystalline (1S)-1-(3-ethoxy-4-methoxyphenyl)-2-(methylsulfonyl) ethenamine-N-acetyl-L-valine salt of formula (VII).

Figure 1:
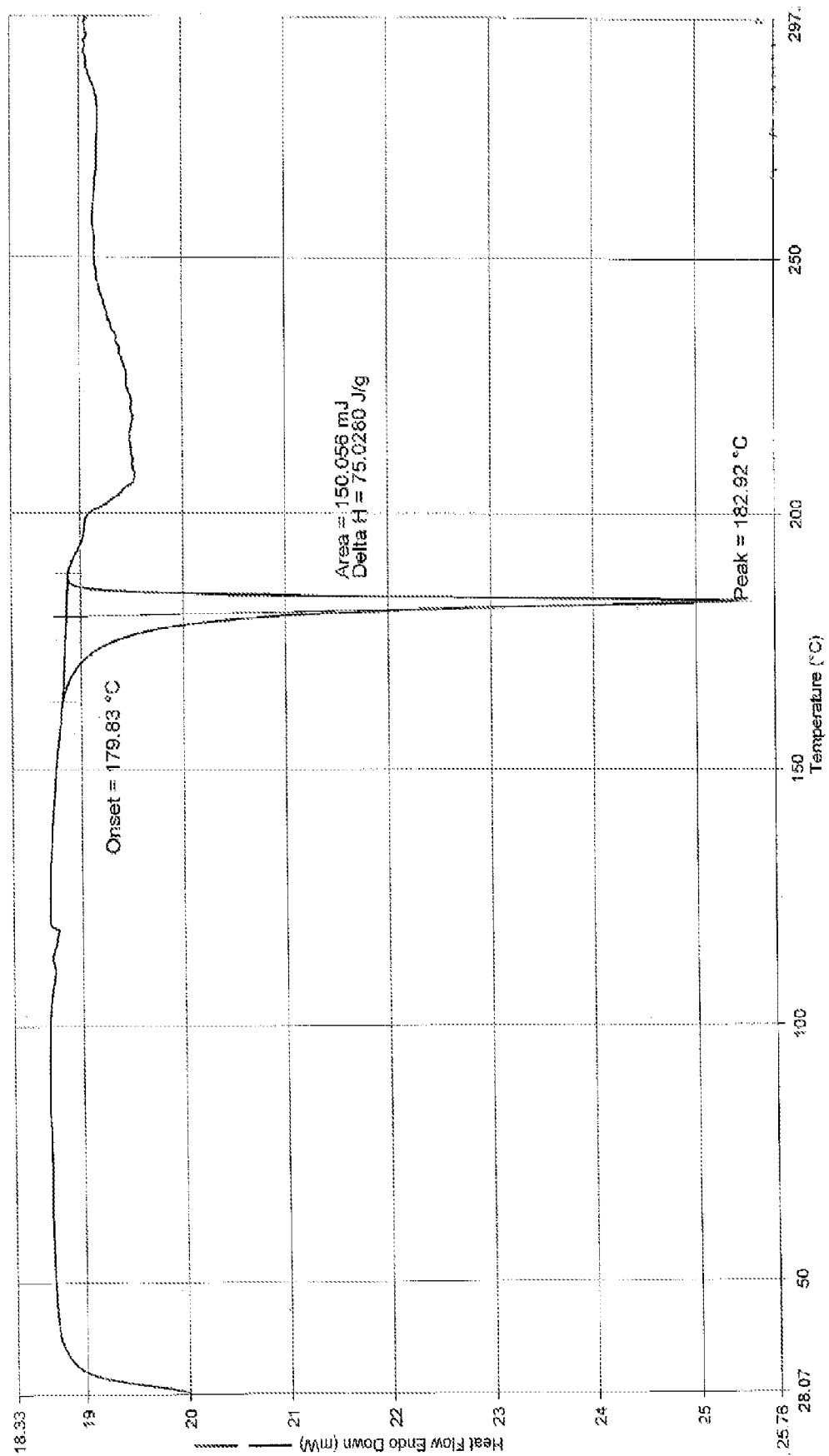

FIG. III: lists the data of the powder X-ray diffraction pattern of crystalline (1S)-1-(3-ethoxy-4-methoxyphenyl)-2-(methylsulfonyl) ethenamine-N-acetyl-L-valine salt of formula (VII).

DETAILED DESCRIPTION OF THE INVENTION

The main embodiment, of the present invention provides an improved process for the preparation of Apremilast of formula (I) as shown in the scheme-I given below:

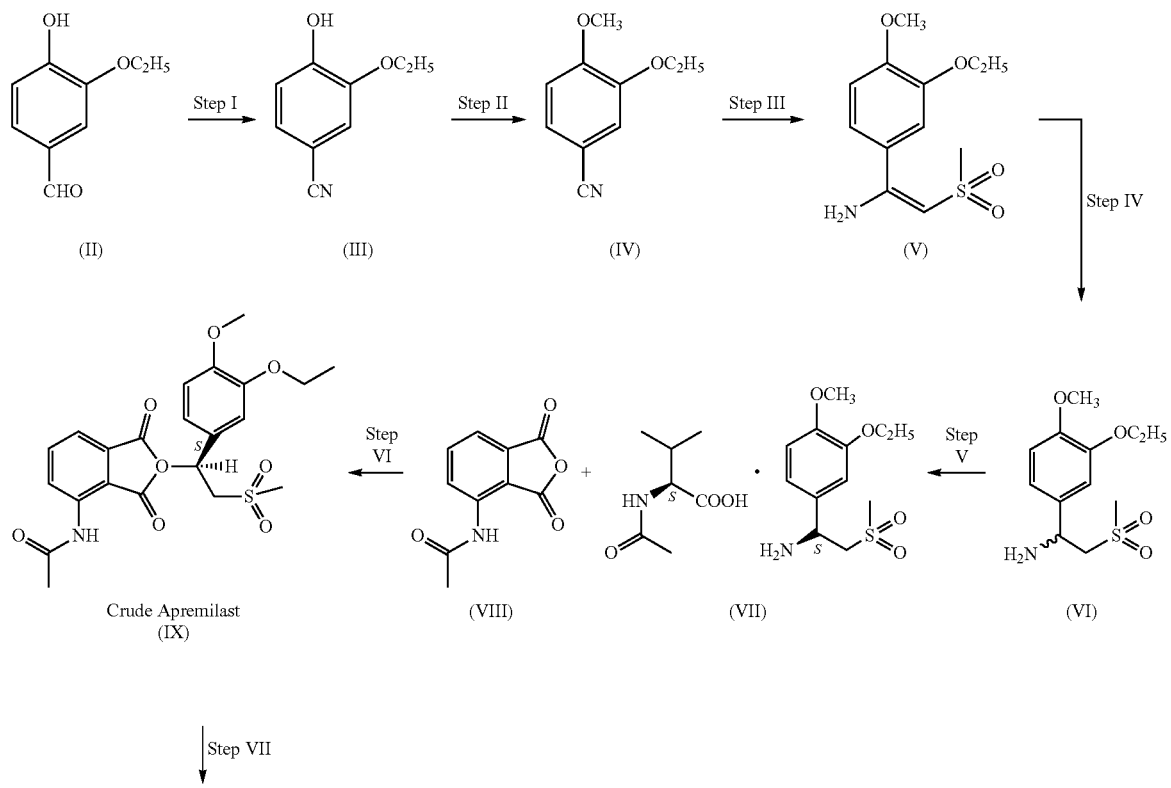

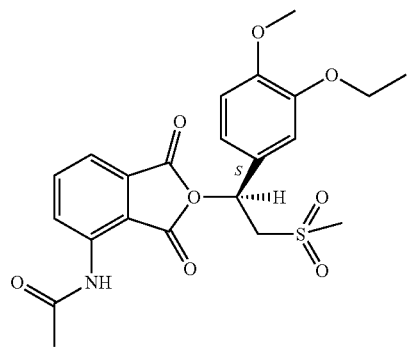

Apremilast
(I)

Step I:

Reacting ethyl vanillin of formula (II) with hydroxylamine, or a salt thereof in a solvent to obtain 3-ethoxy-4-hydroxybenzonitrile of formula (III);

The solvent used in the reaction is selected from acetonitrile, ethyl acetate, acetone, methyl ethyl ketone, diethyl ether, tetrahydrofuran, dichloromethane, chloroform, N-methylpyrrolidinone, dimethyl formamide, dimethyl sulfoxide, formic acid, acetic acid, and mixtures thereof; preferably the solvent used is acetonitrile.

The reaction temperature may range from 70° C. to 90° C. and preferably at a temperature in the range from 70° C. to 85° C. The duration of the reaction may range from 3 hour to 5 hours, preferably for a period of 4 hours.

Step II:

Methylating 3-ethoxy-4-hydroxybenzonitrile of formula (III) with o-methylating reagent in a solvent in the presence of a base to obtain 3-ethoxy-4-methoxybenzonitrile of formula (IV);

The O-methylating reagent used in the reaction is selected from methyl iodide, dimethyl sulfate, diazomethane, methyl triflate, dimethyl carbonate, diazomethane or tri methyl silyl diazomethane; preferably methyl iodide.

The solvent used in the reaction is selected from acetone, ethylmethyl ketone, ethylisobutyl ketone, acetonitrile, ethyl acetate, isopropyl acetate, tetrahydrofuran, toluene, xylene, Dimethyl formamide, dimethyl sulfoxide or cyclohexane; preferably the solvent used is acetone.

The base used in the reaction is selected from potassium carbonate, potassium bicarbonate, sodium bicarbonate, caesium carbonate, caesium bicarbonate, sodium hydroxide, potassium hydroxide or sodium carbonate; preferably the base used is potassium carbonate.

The reaction temperature may range from 45° C. to 65° C. and preferably at a temperature in the range from 50° C. to 60° C. The duration of the reaction may range from 3 hour to 5 hours, preferably for a period of 4 hours.

Step III:

Reacting 3-ethoxy-4-methoxybenzonitrile of formula (IV) with dimethyl sulfone and n-BuLi in hexane in a solvent to obtain (E/Z)-1-(3-ethoxy-4-methoxyphenyl)-2-(methylsulfonyl) ethenamine of formula (V);

The solvent used in the reaction is selected from tetrahydrofuran, methyl tetrahydrofuran, diethyl ether, N-methyl pyrrolidone, Methyl tert-butyl ether (MTBE), glyme, diglyme, toluene, xylene, hexanes and mixtures thereof; preferably the solvent used is tetrahydrofuran.

The reaction temperature may range from 0° C. to 10° C. and preferably at a temperature in the range from −5 to +5° C. The duration of the reaction may range from 30 minutes to 2 hours, preferably for a period of 1 hour.

Step IV:

Reducing (E/Z)-1-(3-ethoxy-4-methoxyphenyl)-2-(methylsulfonyl) ethenamine of formula (V) with reducing agent and chiral auxiliary in a solvent to obtain 1-(3-ethoxy-4-methoxyphenyl)-2-(methylsulfonyl) ethanamine of formula (VI);

The solvent used in the reaction is selected from tetrahydrofuran, methyl tetrahydrofuran, ethyl acetate, methanol, ethanol, toluene, dichloromethane, chloroform or mixture thereof; preferably the solvent used is tetrahydrofuran.

The reducing agent used in the reaction is selected from combination of sodium borohydride and boron trifluoride diethyl etherate, sodium borohydride and titanium tetrachloride, sodium borohydride and zinc dichloride, sodium borohydride, ferric chloride, potassium borohydride and boron trifluoride diethyl etherate, potassium borohydride and titanium tetrachloride, potassium borohydride and zinc dichloride, potassium borohydride and ferric chloride, lithium borohydride and boron trifluoride diethyl etherate, lithium borohydride and titanium tetrachloride, lithium borohydride and zinc dichloride or lithium borohydride and ferric chloride; preferably the reducing agent used is combination of sodium borohydride and boron trifluoride diethyl etherate.

The chiral auxiliary used in the reaction is selected from L-valinol, L-valine, L-leucine, L-proline, L-pyroglutamic acid, L-madelic acid, L-tartaric acid, L-phenyl alanine, L-phenyl glycine or L-Camphorsulfonic acid; preferably the chiral auxiliary used is L-valinol.

The reaction temperature may range from −15° C. to 5° C. and preferably at a temperature in the range from −10° C. to −5° C. The duration of the reaction may range from 1 hour to 4 hours, preferably for a period of 2 hours to 3 hours.

Step V:

Reacting 1-(3-ethoxy-4-methoxyphenyl)-2-(methylsulfonyl) ethanamine of formula (VI) with N-acetyl-L-valine in a solvent to obtain (1S)-1-(3-ethoxy-4-methoxyphenyl)-2-(methylsulfonyl) ethanamine-N-acetyl-L-valine salt of formula (VII) having chiral purity greater than 99.8%;

The solvent used in the reaction is selected from methanol, ethanol, isopropanol, water, propanol, butanol, DMF, DMSO, isobutyl alcohol any one of or mixture thereof; preferably the solvents used are ethanol, isopropanol, water or their mixtures.

The reaction temperature may range from 40° C. to 80° C. and preferably at a temperature of 50° C. to 70° C. The duration of the reaction may range from 30 minutes to 1 hour, preferably for a period of 1 hour.

Step VI:

Reacting (1S)-1-(3-ethoxy-4-methoxyphenyl)-2-(methylsulfonyl) ethenamine-N-acetyl-L-valine salt of formula (VII) with 3-acetamidophthalic anhydride of formula (VIII) in the presence of acetic acid in a solvent to obtain crude Apremilast of Formula (IX);

The solvent used in the reaction is selected from tetrahydrofuran, methyl tetrahydrofuran, ethyl acetate, methanol, ethanol, toluene, dichloromethane, chloroform any one of or mixture thereof; preferably the solvent used is tetrahydrofuran.

The reaction temperature may range from 50° C. to 130° C. and preferably at a temperature of 60° C. to 125° C. The duration of the reaction may range from 5 hours to 9 hours, preferably for a period of 6 hours to 8 hours.

After completion of the reaction, acetic anhydride is added to the reaction mixture at a temperature of 20 to 50° C. and preferably at a temperature of 25 to 35° C. to convert amino impurity of formula (X)

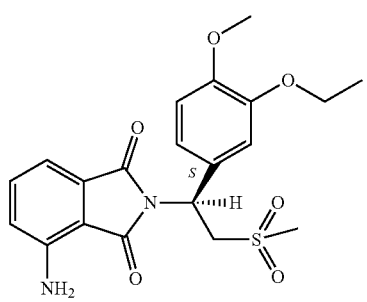

(X)

to obtain crude Apremilast of Formula (IX).

Step VII:

Purifying crude Apremilast of formula (IX) with mixed solvent to obtain Apremilast of formula (I).

The mixed solvent used in the reaction is ethanol and acetone. The reaction temperature may range from 40° C. to 70° C.; preferably at a temperature in the range from 50° C. to 60° C. The duration of the reaction may range from 3 hours to 5 hours, preferably for a period of 4 hours.

In a preferred embodiment, the present invention provides an improved process for the preparation of Apremilast of formula (I).

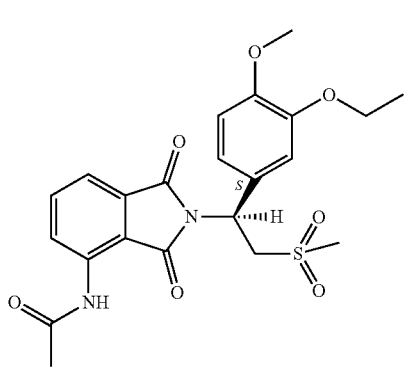

(I)

which comprises:

i) reacting ethyl vanillin of formula (II)

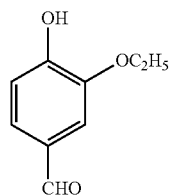

(II)

with hydroxylamine hydrochloride in acetonitrile to obtain 3-ethoxy-4-hydroxybenzonitrile of formula (III);

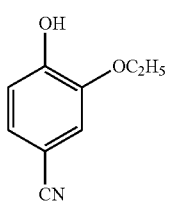

(III)

ii) methylating 3-ethoxy-4-hydroxybenzonitrile of formula (III) with methyl iodide in acetone in the presence of potassium carbonate to obtain 3-ethoxy-4-methoxybenzonitrile of formula (IV);

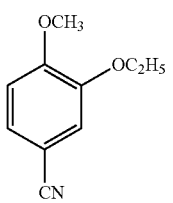

(IV)

iii) reacting 3-ethoxy-4-methoxybenzonitrile of formula (IV) with dimethyl sulfone and n-BuLi in hexane in tetrahydrofuran to obtain (E/Z)-1-(3-ethoxy-4-methoxyphenyl)-2-(methylsulfonyl) ethenamine of formula (V);

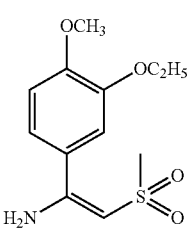

(V)

iv) reducing (E/Z)-1-(3-ethoxy-4-methoxyphenyl)-2-(methylsulfonyl) ethenamine of formula (V) with sodium borohydride, boron trifluoride etherate and L-valinol in tetrahydrofuran to obtain 1-(3-ethoxy-4-methoxyphenyl)-2-(methylsulfonyl) ethanamine of formula (VI);

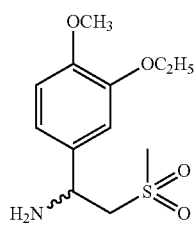
(VI)

v) reacting 1-(3-ethoxy-4-methoxyphenyl)-2-(methylsulfonyl) ethanamine of formula (VI) with N-acetyl-L-valine in ethanol, water and isopropyl alcohol to obtain (1S)-1-(3-ethoxy-4-methoxyphenyl)-2-(methylsulfonyl) ethenamine-N-acetyl-L-valine salt of formula (VII);

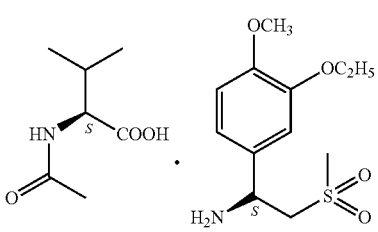
(VII)

vi) reacting (1S)-1-(3-ethoxy-4-methoxyphenyl)-2-(methylsulfonyl) ethenamine-N-acetyl-L-valine salt of formula (VII) with 3-acetamino phthalic anhydride of formula (VIII)

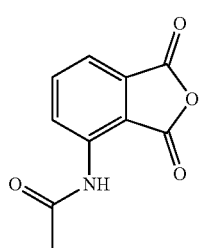
(VIII)

in the presence of acetic acid in tetrahydrofuran to obtain crude Apremilast of formula (IX);

vii) Purifying crude Apremilast of Formula (IX) with ethanol and acetone to obtain Apremilast of formula (I).

In another preferred embodiment, the present invention provides a novel process for the preparation of 3-ethoxy-4-methoxybenzonitrile of formula (IV)

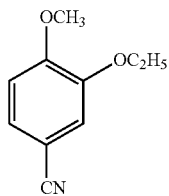
(IV)

which comprises:
methylating 3-ethoxy-4-hydroxybenzonitrile of formula (III)

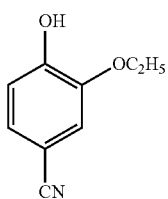
(III)

with O-methylating reagent in a solvent in the presence of a base to obtain 3-ethoxy-4-methoxybenzonitrile of formula (IV).

In another preferred embodiment, the present invention provides a novel process for the preparation of 3-ethoxy-4-methoxybenzonitrile of formula (IV)

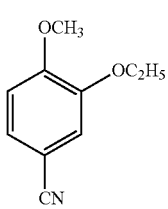
(IV)

which comprises:
methylating 3-ethoxy-4-hydroxybenzonitrile of formula (III)

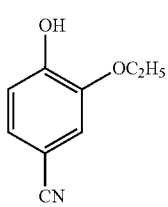
(III)

with methyl iodide in acetone in the presence of potassium carbonate to obtain 3-ethoxy-4-methoxybenzonitrile of formula (IV).

In another preferred embodiment, the present invention provides an improved process for the preparation of 1-(3-ethoxy-4-methoxyphenyl)-2-(methylsulfonyl) ethanamine of formula (VI)

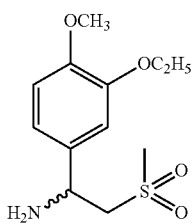
(VI)

which comprises:
reducing (E/Z)-1-(3-ethoxy-4-methoxyphenyl)-2-(methylsulfonyl) ethenamine of formula (V)

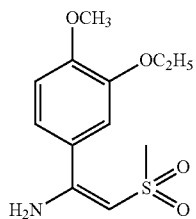

(V)

with reducing agent & chiral auxiliary in a solvent to obtain 1-(3-ethoxy-4-methoxyphenyl)-2-(methylsulfonyl) ethanamine of formula (VI).

In another preferred embodiment, the present invention provides an improved process for the preparation of 1-(3-ethoxy-4-methoxyphenyl)-2-(methylsulfonyl) ethanamine of formula (VI)

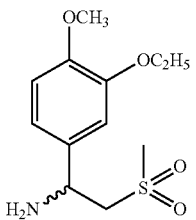

(VI)

which comprises:

reducing (E/Z)-1-(3-ethoxy-4-methoxyphenyl)-2-(methylsulfonyl) ethanamine of formula (V)

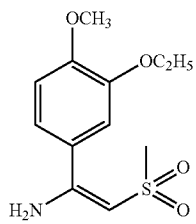

(V)

with sodium borohydride and boron trifluoride etherate; and L-valinol in tetrahydrofuran to obtain 1-(3-ethoxy-4-methoxyphenyl)-2-(methylsulfonyl) ethanamine of formula (VI).

In further preferred embodiment, crystalline form of (1S)-1-(3-ethoxy-4-methoxyphenyl)-2-(methylsulfonyl) ethenamine-N-acetyl-L-valine salt having the following structural formula (VII)

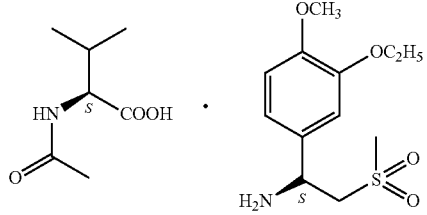

(VII)

characterized by its powder X-ray diffraction peaks at 18.3, 14.4, 9.8, 9.5, 8.1, 7.6, 6.2, 5.8, 5.5, 5.1, 4.9, 4.8, 4.6, 4.3, 4.2, 4.0, 3.8, 3.7, 3.5, 3.3, 3.2, 3.1, 3.0, 2.8, 2.7, 2.6, 2.4, 2.2 and 1.9±0.2 degrees 2θ.

The following examples are provided to enable one skilled in the art to practice the invention and merely illustrate the process of the invention. However, it is not intended in any way to limit the scope of the present invention.

EXAMPLES

Example-1: Preparation of 3-ethoxy-4-hydroxybenzonitrile

To the round bottom flask, charge Ethyl vanillin (100.0 grams, 0.602 mol), hydroxylamine hydrochloride (50.2 grams, 0.722 mol), and acetonitrile (300 mL). The stirred slurry was heated to reflux for 4 hours. The stirred mixture was allowed to cool at 40-45° C. and distilled off acetonitrile under vacuum. Water (500 mL) was charged to reaction mass and extract with ethyl acetate (2×300 mL). The combined ethyl acetate layer was washed with 10% sodium chloride solution (200 mL). The ethyl acetate layer was distilled off under vacuum at 40-45° C. Reaction mass was co-distilled with n-hexane (100 mL). Cool the reaction mass at 25-30° C. and charge n-hexane (200 mL). The isolated solid was filtered and wash with n-hexane (50 mL) and dried in vacuum oven at 35-40° C. to a constant weight, yielding 93.3 grams (95.2%) of 3-ethoxy-4-hydroxybenzonitrile as light yellow solid.

$^1$H NMR (DMSO-d$^6$) δ: 1.34 (t, 3H), 4.08 (q, 2H), 6.92 (d, 1H), 7.25 (m, 1H), 7.31 (s, 1H), 10.17 (s, 1H) ppm;

FT IR (KBr): 617, 1026, 1287, 1518, 1599, 2225, 3228, 3378 cm$^{-1}$;

MS (ESI) m/z=164.10 (M+1).

Example-2: Preparation of 3-ethoxy-4-methoxybenzonitrile

A 2 L 3-necked round bottom flask was equipped with a mechanical stirrer, thermometer, and condenser, charge 3-ethoxy-4-hydroxybenzonitrile (90.0 grams, 0.551 mol), potassium carbonate (152.2 grams, 1.103 mol), methyl iodide (97.2 grams, 0.689 mol) and acetone (900 mL). The stirred slurry was heated to reflux for 4 hours. The stirred mixture was allowed to cool at 35-40° C. and distilled off acetone under vacuum. Water (450 mL) was charge to reaction mass and extract with ethyl acetate (2×450 mL). The combined ethyl acetate layer was washed with 10% sodium bicarbonate solution (180 mL) followed by sodium chloride solution (180 mL). The ethyl acetate layer was distilled out under vacuum at 40-45° C. Co-distilled with n-hexane (90 mL). Cool reaction mass at 25-30° C. and charge n-hexane (180 mL). The isolated solid was filtered and wash with n-hexane (45 mL) and dried in vacuum oven at 40-45° C. to a constant weight, yielding 87.2 grams (89.3%) of 3-ethoxy-4-methoxybenzonitrile as off white solid.

$^1$H NMR (CDCl$_3$) δ: 1.51 (t, 3H), 3.92 (s, 3H), 4.14 (q, 2H), 6.92, (d, 1H), 7.08 (d, 1H), 7.29 (dd, 1H) ppm;

FT IR (KBr): 1266, 1517, 1589, 2228, 2941, 2981 cm$^{-1}$;

MS (ESI) m/z=178.13 (M+1);

DSC (onset): 69.10° C.

Example 3: Preparation of (E/Z)-1-(3-ethoxy-4-methoxyphenyl)-2-(methylsulfonyl) ethenamine To a 3 L round bottom flask equipped with a mechanical stirrer, thermometer, and condenser, charge dry THF (600 mL), dimethyl sulfone (106.3 grams, 1.13 mole) followed by 1.6 M n-butyl lithium in hexane (704 mL, 1.13 mole) at −5 to 0° C. within 1 hour. The resulting mixture was agitated for 1 hour then a solution of 3-ethoxy-4-methoxybenzonitrile (100 grams, 0.565 mole) in tetrahydrofuran (THF) (300 mL) was added at −5 to 0° C. within 30-45 minutes. The mixture was agitated at 0-5° C. for 1 hour, warmed to 25-30° C. and stirred for overnight. After thin layer chromatography (TLC) complies distilled out THF under vacuum. Add water (1000 mL) and ethyl acetate (500 mL) to reaction mass. Extract the aqueous layer again with ethyl acetate (300 mL). The combined ethyl acetate layer was washed with brined solution (300 mL). Distilled off ethyl acetate under vacuum and charge n-hexane (300 mL) to the crude solid and filter the isolated solid on Buchner funnel. The solid was dried under reduced pressure at 40-45° C. to provide (E/Z)-1-(3-ethoxy-4-methoxyphenyl)-2-(methylsulfonyl) ethenamine as a light yellow solid (147 grams, 96% yield).

$^1$H NMR (CDCl$_3$) δ: 1.36 (t, 3H), 2.99 (s, 3H), 3.79 (s, 3H), 4.11 (q, 2H), 5.02 (s, 1H), 6.82 (bs, 2H), 7.02 (d, 1H), 7.19 (m, 2H) ppm;

MS (ESI) m/z=272.15 (M+1);

FT IR (KBr) 963, 1099, 1262, 1517, 1551, 1639, 3347, 3448 cm$^{-1}$.

Example 4: Preparation of 1-(3-ethoxy-4-methoxyphenyl)-2-(methylsulfonyl) ethanamine To a 2 L round bottom flask equipped with a mechanical stirrer, thermometer, and condenser, charge 500 mL of THF followed by (E/Z)-1-(3-ethoxy-4-methoxyphenyl)-2-(methylsulfonyl) ethenamine (50 grams, 0.184 mole) at 25-30° C. The mixture was cooled at −10° C. to 0° C. Charge sodium borohydride (8.36 grams, 0.221 mole) and L-valinol (4.7 grams, 0.046 mole) to reaction mass and stir for 1 hour at −10° C. to 0° C. To the cooled the reaction mass add mixture of Borontrifluoride diethyl etherate (28.56 mL, 0.221 moles) in THF (30 mL) in 1 hour at −10 to 0° C. The mixture was allowed to warm at 25-30° C. in 2-3 hours and stirred overnight at 25-30° C. Water (250 mL) was charged to reaction mass at 0-10° C. After warming to 25-30° C., the THF was distilled out from reaction mixture under vacuum. Charge ethyl acetate (200 mL) to reaction mass and add concentrated Hydrochloric acid (50 mL) till pH 2-3. Separate the organic and aqueous layer. To the aqueous layer charge 30% sodium hydroxide (225 mL) till pH 10-11. Extract the compound by using dichloromethane (2×250 mL). Club the organic layers and wash with 10% aqueous sodium chloride solution. Distilled off dichloromethane for organic layer. To the crude solid charge THF (25 mL) and stir for 30 minutes. Filter the isolated solid on Buchner funnel. The wet solid dried in hot air oven at 40-45° C. for 4 hours to provide 1-(3-ethoxy-4-methoxyphenyl)-2-(methylsulfonyl)ethanamine as off white solid (41.7 grams, 83% yield).

$^1$H NMR (DMSO-d$^6$) δ 1.35 (t, 3H), 2.09 (bs, 2H), 2.96 (s, 3H), 3.2 (m, 1H), 3.4 (m, 1H), 3.73 (s, 3H), 4.05 (q, 2H), 4.28 (m, 1H), 6.89 (s, 2H), 7.02 (s, 1H) ppm;

FTIR (KBr): 907, 1025, 1142, 1256, 1312, 1517, 1590, 2983, 3362 cm$^{-1}$;

MS (ESI) m/z=274.23 (M+1);

Chiral HPLC: 37.14% (R-Isomer): 62.86% (S-isomer).

Example 5: Preparation of (1S)-1-(3-ethoxy-4-methoxyphenyl)-2-(methylsulfonyl) ethenamine-N-acetyl-L-valine Salt A 500 ml 3-necked round bottom flask was equipped with a mechanical stirrer, thermometer, and condenser, charge 1-(3-ethoxy-4-methoxyphenyl)-2-(methylsulfonyl)ethanamine (40.0 grams, 0.146 mole), N-acetyl-L-valine (17.5 grams, 0.109 mole), and ethanol (120 mL). The stirred slurry was heated to reflux for 1 hour and add water (24 mL) till clear solution. The stirred mixture was allowed to cool at 25° C. and stirring was continued for another 30 minutes at 25° C. The crude solid refluxed with Isopropyl alcohol (110 mL) and add water (30 mL) till clear solution. Cool the solution at 25° C. and filter on Buchner funnel. The wet solid was dried in vacuum oven at 35-40° C. to a constant weight, giving 13.2 grams (41% yield based on S isomer) of (1S)-1-(3-ethoxy-4-methoxyphenyl)-2 (methylsulfonyl) ethenamine-N-acetyl-L-valine salt as white solid.

$^1$H NMR (DMSO-d$^6$) δ: 0.88 (d, 6H), 1.35 (t, 3H), 1.87 (s, 3H), 2.08 (m, 1H), 2.95 9s, 3H), 3.30 (m, 1H), 3.47 (m, 1H), 3.73 (s, 3H), 3.98 (q, 2H), 4.13 (m, 1H), 4.30 (m, 1H), 6.89 (d, 2H), 7.03 (s, 1H), 7.96 (d, 1H) ppm;

FT IR (KBr): 1107, 1296, 1403, 1521, 1572, 1619, 1660, 2963, 3322 cm$^{-1}$;

MS (ESI) m/z=274.17 (M+1 for free base);

PXRD (2θ): 4.82 (100%), 8.98, 9.27, 9.47, 10.92, 11.65, 14.21, 15.14, 16.12, 17.83, 18.13, 18.43, 19.16, 23.56, 24.86, 28.30, 28.45;

DSC: 179.83° C. (Onset).

Example 6: Preparation of N-{2-[(1S)-1-(3-ethoxy-4-methoxyphenyl)-2-(methylsulfonyl)ethyl]-1,3-dioxo-2,3-dihydro-1H-isoindol-4-yl}acetamide [Apremilast]

To a 500 ml round bottom flask equipped with a mechanical stirrer, thermometer, and condenser, charge acetic acid (100 mL) followed by (1S)-1-(3-ethoxy-4-methoxyphenyl)-2 (methylsulfonyl) ethenamine-N-acetyl-L-valine (10 grams, 0.023 mole) at 25-30° C. Stir the mixture for 10 minutes and charge 3-Acetamidophthalic anhydride (4.98 grams, 0.024 mole) at 25-30° C. The mixture was heated at 120° C. for 6-8 hours. The mixture was cooled to 35-40° C., acetic anhydride (5 grams, 0.049 mol) is added to the reaction mixture and stirr for 1 hour at 35-40° C. and remove the solvents under vacuum. Add water (100 mL) and dichloromethane (2×100 mL). Club the organic layers and charge 5% aqueous sodium bicarbonate solution (100 mL) and stir for 15 minutes. Separate the organic and aqueous layer. Distilled off dichloromethane from organic layer. To the crude solid charge n-hexane (30 mL) and stir for 30 min at 25-30° C. Filter the isolated solid on Buchner funnel and wash with 10 mL of n-Hexane. Unload the solid and dry in hot air oven at 40-45° C. for 4-6 hours to provide N-{2-[(1S)-1-(3-ethoxy-4-methoxyphenyl)-2-(methylsulfonyl) ethyl]-1,3-dioxo-2,3-dihydro-1H-isoindol-4-yl}acetamide as light yellow solid (10.1 grams, 94% yield).

$^1$H NMR (DMSO-d$^6$) δ: 9.71 (s, 1H), 8.45 (d, 1H), 7.81 (m, 1H), 7.58 (d, 1H), 7.0 (s, 1H), 6.97 (m, 1H), 5.80 (m, 1H), 4.39 (m, 1H), 4.17 (m, 1H), 4.05 (q, 2H), 3.73 (s, 3H), 3.02 (s, 3H), 2.19 (s, 2H), 1.34 (t, 3H) ppm;

$^{13}$C NMR (DMSO-d$^6$) δ: 14.62, 24.15, 41.04, 47.17, 52.89, 55.48, 63.88, 111.80, 112.44, 116.61, 118.13, 119.72, 126.01, 129.46, 131.31, 135.86, 136.50, 147.88, 148.93, 166.89, 167.82, 169.20 ppm;

FT IR (KBr): 1136, 1393, 1521, 1618, 1704, 1764, 3002, 3362 cm$^{-1}$;

MS (ESI) m/z=459.12 (M–H).

Example 7: Preparation of N-{2-[(1S)-1-(3-ethoxy-4-methoxyphenyl)-2-(methylsulfonyl)ethyl]-1,3-dioxo-2,3-dihydro-1H-isoindol-4-yl}acetamide [Apremilast Form-B]

To a 100 ml round bottom flask equipped with a mechanical stirrer, thermometer, and condenser charge acetone (30 ml) followed by N-{2-[(1S)-1-(3-ethoxy-4-methoxy phenyl)-2-(methylsulfonyl)ethyl]-1,3-dioxo-2,3-dihydro-1H-isoindol-4-yl}acetamide (10 g, 0.022 mol) at 25-30° C. Reflux the mixture for clear solution. Add ethanol (100 ml) to the mixture at 50-55° C. for 1 h. Allow reaction mass to cool at 25-30° C. over 12 h. Solid isolation observed at 35° C. Filter the isolated solid, wash with ethanol (10 ml) and dry the solid in vacuum oven at 50-55° C. for 4-6 h till constant weight to give pure N-{2-[(1S)-1-(3-ethoxy-4-methoxyphenyl)-2-(methylsulfonyl)ethyl]-1,3-dioxo-2,3-dihydro-1H-isoindol-4-yl}acetamide (Apremilast Form-B). Dry Wt.: 7.1 g Yield: 71%.

$^1$H NMR (DMSO-d$^6$) δ: 1.36 (t, 3H), 2.20 (s, 3H), 3.02 (s, 3H), 3.73 (s, 3H), 4.05 (q, 2H), 4.18 (m, 1H), 4.39 (m, 1H), 5.80 (q, 1H), 6.97 (q, 1H), 7.07 (d, 1H), 7.58 (d, 1H), 7.81 (t, 1H), 8.45 (d, 1H), 9.71 (bs, 1H) ppm;

$^{13}$C NMR (DMSO-d$^6$) δ 14.62, 24.15, 41.04, 47.17, 52.89, 55.48, 63.88, 111.80, 112.44, 116.61, 118.13, 119.72, 126.01, 129.46, 131.31, 135.86, 136.50, 147.88, 148.93, 166.89, 167.82, 169.20 ppm;

FT IR (KBr) 1136, 1393, 1521, 1618, 1704, 1764, 3002, 3362 cm$^{-1}$;

MS (ESI) m/z=459.12 (M–H);

XRD (2θ): 6.0, 7.8, 10.1, 12.4, 13.5, 15.7, 16.3, 18.1, 20.7, 22.5, 24.7, 26.2, 26.9, 29.1.

Advantages of the Present Invention

1. Starting raw material (3-ethoxy-4-hydroxy benzaldehyde) is cheaper
2. In step iv), chiral auxiallary is used for high selectivity, to convert (E/Z)-1-(3-ethoxy-4-methoxyphenyl)-2-(methylsulfonyl) ethenamine to 1-(3-ethoxy-4-methoxyphenyl)-2-(methylsulfonyl) ethanamine
4. purification of (S), (S)-1-(3-ethoxy-4-methoxyphenyl)-2-(methylsulfonyl) ethenamine-N-acetyl-L-valine salt is done by using isopropanol, ethanol, methanol, water or mixture thereof to get (S), (S)-1-(3-ethoxy-4-methoxyphenyl)-2-(methylsulfonyl) ethenamine-N-acetyl-L-valine salt with chiral purity >99.8% and (S) (R) 1-(3-ethoxy-4-methoxyphenyl)-2-(methylsulfonyl) ethenamine-N-acetyl-L-valine salt with chiral purity not more than 0.20%.
5. Acetic anhydride is added to the reaction mixture obtained in step (VI) to give crude Apremilast of formula (IX) having free of amine impurity of formula (X).

We claim:
1. An improved process for the preparation of Apremilast of Formula (I)

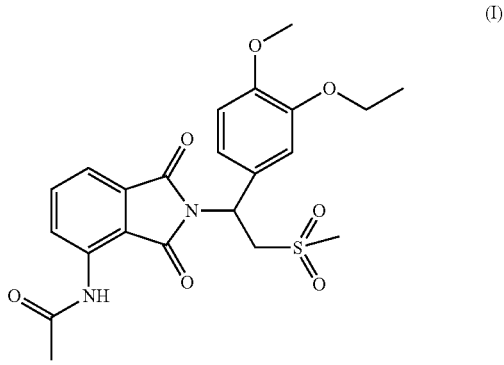 [SMILES: CCOc1cc(C(CS(C)(=O)=O)N2C(=O)c3cccc(NC(C)=O)c3C2=O)ccc1OC]

which comprises:
i) reacting ethyl vanillin of formula (II)

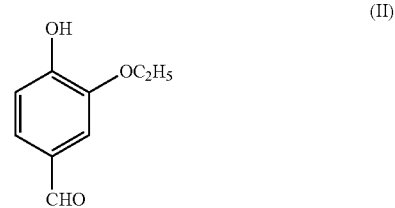 [SMILES: CCOc1cc(C=O)ccc1O]

with hydroxylamine, or salt thereof in a solvent to obtain 3-ethoxy-4-hydroxybenzonitrile of formula (III);

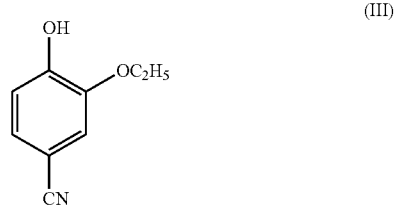 [SMILES: CCOc1cc(C#N)ccc1O]

ii) methylating 3-ethoxy-4-hydroxybenzonitrile of formula (III) with O-methylating reagent in a solvent in the presence of a base to obtain 3-ethoxy-4-methoxybenzonitrile of formula (IV);

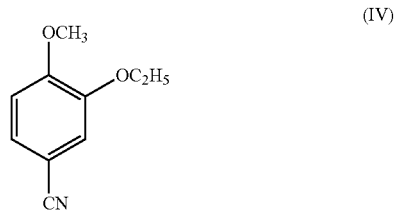 [SMILES: CCOc1cc(C#N)ccc1OC]

iii) reacting 3-ethoxy-4-methoxybenzonitrile of formula (IV) with dimethyl sulfone and n-BuLi in hexane in a solvent to obtain
(E/Z)-1-(3-ethoxy-4-methoxyphenyl)-2-(methylsulfonyl) ethenamine of formula (V);

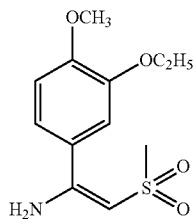

(V)

iv) reducing (E/Z)-1-(3-ethoxy-4-methoxyphenyl)-2-(methylsulfonyl) ethenamine of formula (V) with reducing agent and chiral auxiliary in a solvent to obtain
1-(3-ethoxy-4-methoxyphenyl)-2-(methylsulfonyl) ethanamine of formula (VI);

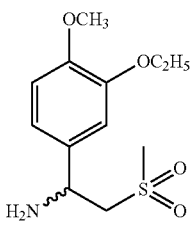

(VI)

v) reacting 1-(3-ethoxy-4-methoxyphenyl)-2-(methylsulfonyl) ethanamine of formula (VI) with N-acetyl-L-valine in a solvent to obtain
(1S)-1-(3-ethoxy-4-methoxyphenyl)-2-(methylsulfonyl) ethenamine-N-acetyl-L-valine salt of formula (VII);

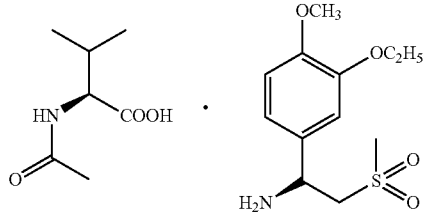

(VII)

vi) reacting (1S)-1-(3-ethoxy-4-methoxyphenyl)-2-(methylsulfonyl) ethenamine-N-acetyl-L-valine salt of formula (VII) with 3-acetamino phthalic anhydride of formula (VIII)

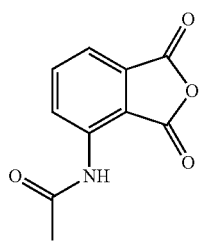

(VIII)

in the presence of acetic acid in a solvent to obtain crude Apremilast; and vii) purifying crude Apremilast with mixed solvent to obtain Apremilast of Formula (I).

2. The process as claimed in claim 1, wherein,
in step i) the solvent is selected from acetonitrile, ethyl acetate, acetone, methyl ethyl ketone, diethyl ether, tetrahydrofuran, dichloromethane, chloroform, N-methylpyrrolidinone, dimethyl formamide, dimethyl sulfoxide, formic acid, acetic acid, or mixtures thereof;
in step ii) the base is selected from potassium carbonate, potassium bicarbonate, sodium bicarbonate, caesium carbonate, caesium bicarbonate, sodium hydroxide, potassium hydroxide, sodium carbonate; the solvent is selected from acetone, ethyl methyl ketone, ethyl isobutyl ketone, acetonitrile, ethyl acetate, isopropyl acetate, tetrahydrofuran, toluene, xylene, dimethyl formamide, dimethyl sulfoxide or cyclohexane; and the O-methylating reagent is selected from methyl iodide, dimethyl sulfate, diazomethane, methyl triflate, dimethyl carbonate, diazomethane or tri methyl silyl diazomethane;
in step iii) the solvent is selected from tetrahydrofuran, methyl tetrahydrofuran, diethyl ether, N-methyl pyrrolidone, Methyl tert-butyl ether (MTBE), glyme, diglyme, toluene, xylene, hexanes or mixtures thereof; and
in step iv) the reducing agent is selected from combination of sodium borohydride and boron trifluoride diethyl etherate, sodium borohydride and titanium tetrachloride, sodium borohydride and zinc dichloride, sodium borohydride, ferric chloride, potassium borohydride and boron trifluoride diethyl etherate, potassium borohydride and titanium tetrachloride, potassium borohydride and zinc dichloride, potassium borohydride and ferric chloride, lithium borohydride and boron trifluoride diethyl etherate, lithium borohydride and titanium tetrachloride, lithium borohydride and zinc dichloride or lithium borohydride and ferric chloride; solvent is selected tetrahydrofuran, methyl tetrahydrofuran, ethyl acetate, methanol, ethanol, toluene, dichloromethane, chloroform or mixture thereof; and chiral auxiliary is selected from L-valinol, L- valine, L-leucine, L-proline, L-pyroglutamic acid, L-madelic acid, L-tartaric acid, L-phenyl alanine, L-phenyl glycine or L-champho sulfonic acid.

3. The process as claimed in step (ii) of claim 1, wherein base used is potassium carbonate and the solvent used is acetone.

4. The process as claimed in step (iv) of claim 1, wherein chiral auxiliary used is L-valinol.

5. The process for the preparation of 3-ethoxy-4-methoxybenzonitrile of formula (IV) as claimed in step ii) of claim 1,

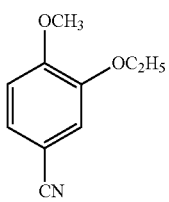

(IV)

which comprises:
methylating 3-ethoxy-4-hydroxybenzonitrile of formula (III)

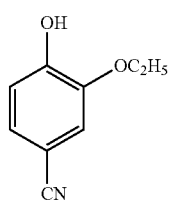

with methyl iodide in acetone in the presence of potassium carbonate to obtain 3-ethoxy-4-methoxybenzonitrile of formula (IV).

6. The process for the preparation of 1-(3-ethoxy-4-methoxyphenyl)-2-(methylsulfonyl) ethanamine of formula (VI) in step iii) of claim 1,

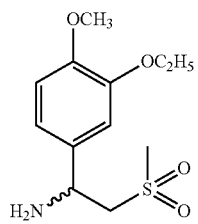

which comprises:
reducing (E/Z)-1-(3-ethoxy-4-methoxyphenyl)-2-(methylsulfonyl) ethenamine of formula (V)

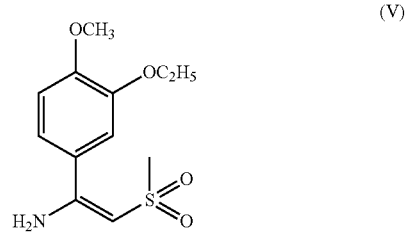 [SMILES: CCOc1cc(/C(N)=C\S(C)(=O)=O)ccc1OC]

with mixture of sodium borohydride and boron trifluoride diethyl etherate and L-valinol in tetrahydrofuran obtain 1-(3-ethoxy-4-methoxyphenyl)-2-(methylsulfonyl) ethanamine of formula (VI).

* * * * *